United States Patent

Benazzi et al.

[11] Patent Number: 5,817,907
[45] Date of Patent: Oct. 6, 1998

[54] PROCESS FOR SKELETAL ISOMERIZATION OF LINEAR OLEFINS USING A PRETREATED MOLECULAR SIEVE, AND A CATALYST CONTAINING A PRETREATED SIEVE

[75] Inventors: Eric Benazzi, Montesson; Michel Guisnet, Buxerolles; Christine Travers, Rueil Malmaison; Ngi Suor Gnep, Bignoux; Patricia Andy, Poitiers, all of France

[73] Assignee: Institut Francais du Petrole, France

[21] Appl. No.: 642,191

[22] Filed: May 6, 1996

[30] Foreign Application Priority Data

May 4, 1995 [FR] France ................................. 95/05463

[51] Int. Cl.$^6$ ..................................................... C07C 5/27
[52] U.S. Cl. ............................................................. 585/671
[58] Field of Search ............................................... 585/671

[56] References Cited

U.S. PATENT DOCUMENTS

| | | | |
|---|---|---|---|
| 4,508,836 | 4/1985 | Haag et al. | 502/53 |
| 5,158,670 | 10/1992 | Cody et al. | 208/120 |
| 5,234,875 | 8/1993 | Han et al. | 502/77 |
| 5,292,984 | 3/1994 | Gajda et al. | 585/667 |
| 5,414,183 | 5/1995 | Abrevaya et al. | 585/671 |
| 5,489,726 | 2/1996 | Huss, Jr. et al. | 585/671 |
| 5,510,559 | 4/1996 | Barger et al. | 585/664 |
| 5,510,560 | 4/1996 | O'Young et al. | 585/671 |
| 5,648,584 | 7/1997 | Murray | 585/666 |

FOREIGN PATENT DOCUMENTS

| | | |
|---|---|---|
| 0 134 076 | 3/1983 | European Pat. Off. . |
| 0 111 808 | 6/1984 | European Pat. Off. . |

*Primary Examiner*—Elizabeth D. Wood
*Attorney, Agent, or Firm*—Millen, White, Zelano & Branigan, P.C.

[57] ABSTRACT

The invention concerns a process for skeletal isomerization of linear olefins using a catalyst containing at least one pre-treated molecular sieve selected from the group formed by SAPO-31, SAPO-11, Theta-1, EU-1, omega zeolite, mordenite, Nu-10, Nu-86, Nu-87, ferrierite, ZSM-12 and ZSM-23. The pre-treatment process consists in bringing the molecular sieve, which has a pore size of 0.4 to 0.8 nm, into contact with at least one hydrocarbon molecule containing 4 to 20 carbon atoms, at a space velocity of 0.1–45 $h^{-1}$, a temperature of 300°–550° C. and at a pressure of 0.1–1 MPa, for 0.5–48 h, to deposit coke in the pores. The process is of particular application to one-dimensional sieves. It is preferably carried out outside the reaction zone. The invention also concerns a catalyst containing a pre-treated sieve, the sieve being selected from SAPO-31, SAPO-11, Theta-1, EU-1, omega zeolite, mordenite, ferrierite, Nu-10, Nu-86 and Nu-87.

19 Claims, No Drawings

PROCESS FOR SKELETAL ISOMERIZATION OF LINEAR OLEFINS USING A PRETREATED MOLECULAR SIEVE, AND A CATALYST CONTAINING A PRETREATED SIEVE

The invention concerns a process for skeletal isomerization of linear olefins using a sieve which has a pore size in the range 0.4 nm to 0.8 nm and which has been pre-treated by coking to render it selective.

The invention also concerns a catalyst containing a sieve selected from the group formed by SAPO-31, SAPO-11, Theta-1, EU-1, omega zeolite, mordenite, ferrierite, Nu-10, Nu-86 and Nu-87, which has been pre-treated by coking to render it selective.

BACKGROUND OF THE INVENTION

Processes for treatment by coking have already been described for catalysts used for aromatic alkylation or isomerization, or for the oligomerisation of olefins.

U.S. Pat. No. 4,508,836 describes a treatment process applied to a catalyst used to convert aromatic feeds by alkylation or isomerization, the catalyst containing a zeolite with a constraint index in the range 1 to 12, particularly ZSM-5, -11, -12, -35 or -38. The treatment described involves bringing the catalyst into contact with an aromatic compound (toluene), optionally in the presence of hydrogen, at a temperature of less than 650° C., deposit more than 1% of coke.

U.S. Pat. No. 5,234,875 describes a catalyst used for oligomerisation of olefins, which contains a ZSM-23 and which has been pre-coked with an olefin, at a temperature of 200°–500° C. and at a pressure of more than 27 bars.

In the present invention, oligomerisation of the olefins (i.e., polymerisation), which would reduce the yield, must be avoided.

Because of the reduction in the level of lead alkyls in fuel over the past few years, the refiner has had to plan to incorporate different compounds into the fuel, in particular alcohols and ethers, to increase the octane number. In addition to methanol which is one of the most important known additives, MTBE (methyl-tertiobutylether) possesses antiknock properties which improve fuel quality and increase the octane number by a greater amount than that obtained with methanol. MTBE has other advantages, such as:

- a boiling point which corresponds to that of the petrol components with the poorest antiknock properties;
- a vapor pressure which is compatible with those components;
- an excellent freezing point;
- low solubility in water;
- complete miscibility with hydrocarbons, etc.

MTBE is generally obtained from isobutene and methanol in the following reaction:

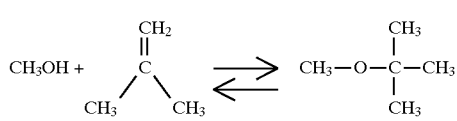

Isobutene is generally contained in olefinic $C_3$–$C_4$ cuts from effluents from catalytic cracking, steam cracking, thermal cracking and visbreaking. However, the quantities of isobutene produced by these different processes are not sufficient to allow large scale development of the MTBE production process.

For this reason, in order to produce larger quantities of isobutene, it has been suggested that the butenes contained in the effluents from the above processes should be completely or almost completely isomerized.

A number of processes associated with a number of catalysts have been proposed in the literature.

Those catalysts are generally based on alumina or on molecular sieves.

A number of catalysts for isomerisation of olefins, more precisely butene to isobutene, incorporate molecular sieves with two-or three-dimensional microporous networks where the channels are interconnected. Those sieves can be associated with a metal "hydrogenating" function such as platinum, palladium or gallium. The main drawbacks of this type of catalyst are:

- deactivation due to the formation of a large quantity of coke;
- formation of unwanted products such as dimers and trimers of butenes and aromatic compounds.
- The term "molecular sieve" means zeolites, i.e., crystalline microporous aluminosilicates, which may be synthetic or natural, also other molecular sieves such as silicoaluminophosphates, SAPO U.S. Pat. No. 4,440,871, aluminophosphates and their derivatives with a metal integrated therein, i.e., MeAPOs and ELAPOs, also silicoaluminophosphates with a metal integrated therein, i.e., MeAPSOs, or ELAPSOs.

More recently, it has been shown that zeolites or molecular sieves containing a one-dimensional microporous network where the pore opening is greater than 0.42 nm and less than 0.7 nm (European patents EP 523,838, EP 501,577) can constitute the active phases in catalysts for the skeletal isomerization of linear olefins.

The structures cited in the above patents are ferrierite, SAPO-11 and a mordenite which has been exchanged with magnesium.

SUMMARY OF THE IVENTION

During studies aimed at improving the performance of these catalysts, it was surprisingly discovered that a molecular sieve which preferably contained a one-dimensional microporous network with a pore size in the range 0.4 nm to 0.8 nm which had undergone a coking pre-treatment under precise conditions to partially or almost completely block the microporous volume led to improved selectivity towards iso-olefins (for example isobutene) during skeletal isomerization of olefins (for example n-butenes). These catalysts also have good catalytic stabilities.

One object of the invention is to provide a skeletal isomerization process using a catalyst containing at least one molecular sieve with a pore size in the range 0.4 nm to 0.8 nm, in which prior to commencing the process, said sieve has been brought into contact with at least one hydrocarbon molecule containing 4 to 20 carbon atoms at a space velocity of 0.1–45 $h^{-1}$, a temperature of 300°–550° C. and at a pressure of 0.1–1 MPa for 0.5–48 h, to deposit coke in said pores of said sieve.

The present invention advantageously concerns molecular sieves with a pore size in the range 0.4 nm to 0.7 nm, and which preferably has a one-dimensional microporous network. Non limiting and non exhaustive examples of molecular sieves which can be treated using the process of the invention are: ferrierite (structure type FER), SAPO-31, SAPO-11 (structure 5 type AEL), Theta-1 (structure type TON), EU-1 (structure type EUO), ZSM-12 (structure type MTW), ZSM-23 (structure type MTT), omega zeolite, mordenite, Nu-10, Nu-86 and Nu-87.

The molecular sieve is treated before (preferred) or after forming in a matrix selected from the group which is preferably formed by alumina, magnesia, silica-alumina and natural clays (kaolin, bentonite), and using techniques such as extrusion, pelletization or bowl granulation. Any matrix which is known to the skilled person may be suitable.

The sieve can also be used as it is, without a matrix.

Elements from various groups in the periodic classification may optionally have been introduced.

The coking pre-treatment for the molecular sieve, formed with or without a binder, is carried out by introducing at least one hydrocarbon molecule containing 4 to 20 carbon atoms, preferably 4 to 12 carbon atoms, preferably selected from the group formed by monoolefins, polyolefins or alkanes, preferably alkanes containing 4 to 12 carbon atoms. The size of this molecule is such that it can penetrate into the interior of the microporosity of the sieve.

Pre-treatment can also be effected by introducing the feed to be converted if it contains the cited molecule(s). This pre-treatment can thus advantageously be effected before the actual start of the conversion reaction.

This is the case when linear olefins are isomerized.

Pre-treatment takes place prior to the isomerization reaction, i.e., on the sieve alone which is the catalyst, or on the sieve alone before forming the catalyst, or on the catalyst containing the sieve.

The process takes place at a space velocity in the range 0.1 $h^{-1}$ to 45 $h^{-1}$, preferably in the range 0.5 $h^{-1}$ to 25 $h^{-1}$, more preferably in the range 0.5 $h^{-1}$ to 10 $h^{-1}$, at a temperature in the range 300° C. to 550° C., preferably in the range 400° C. to 550° C., and advantageously more than 400° C. to 535° C., for a period in the range 0.5 h to 48 h, preferably in the range 0.5 h to 24 h, at a pressure of 0.1–1 MPa, more advantageously 0.1–0.5 MPa.

The feed used for pre-treatment, containing at least one hydrocarbon molecule containing 4 to 20 carbon atoms, is advantageously diluted, for example with an inert gas (nitrogen etc.). The process is carried out in the absence of hydrogen.

After this treatment, the coke content in the molecular sieve is such that the pore volume which is accessible to nitrogen and measured by nitrogen adsorption is in the range 3% to 30% of the pore volume of the uncoked starting sieve, preferably in the range 5% to 20% and more preferably in the range 5% to 15% of the pore volume of the non-coked starting molecular sieve. This test shows that coking occurs in the pores and not solely on the external surface.

This pre-treatment leads to a considerable increase in the selectivity of the catalyst, in particular for skeletal isomerization of olefins. This increase in selectivity originates from a very marked reduction in the yield of products from the disproportionation of the olefin in the feed and of paraffinic products which results from a transfer of hydrogen from the coke precursors to the reactant. Further, the activity of the molecular sieve is hardly changed by the pre-treatment of the invention.

This process can produce improved performance, in particular as regards sieve and/or catalyst stability.

The process described here is preferably carried out in the reaction zone, in a reaction pre-zone or preferably in a dedicated plant provided with the necessary equipment. It can also be carried out in the reaction zone.

In the process for skeletal isomerization of a feed containing linear olefinic hydrocarbons containing 4 to 20 carbon atoms in which the feed is brought into contact with a catalyst at a temperature of 150°–500° C., a pressure of 0.01–1 MPa, a space velocity of 0.1–10 $h^{-1}$, the catalyst comprises a molecular sieve which has been pre-treated in accordance with the process described above.

The feed to be isomerized is brought into contact with the catalyst at a temperature in the range 150° C. to 500° C., (preferably in the range 150° C. to 450° C., in particular when the feed is constituted by butenes and/or pentenes), at a pressure in the range 0.01 MPa to 1 MPa absolute (preferably in the range 0.01 MPa to 0.5 MPa absolute in particular when the feed is constituted by butenes and/or pentenes). The space velocity is in the range 0.1 $h^{-1}$ to 10 $h^{-1}$, expressed as the volume of olefinic feed per volume of catalyst per hour (preferably in the range 0.5 $h^{-1}$ to 6 $h^{-1}$ in particular when the feed is constituted by butenes and/or pentenes).

With the process of the invention, it is possible to isomerize an olefinic $C_4$ cut alone (after removing the $C_3$ cut), the whole of an olefinic $C_3$–$C_4$ cut, an olefinic $C_5$ Cut or more generally, linear olefinic hydrocarbons containing 4 to 20 carbon atoms per molecule, i.e., cuts containing mainly these hydrocarbons.

The catalyst contains 5–100% of sieve, preferably 10–90% by weight of sieve, advantageously 20–80%, the matrix preferably being alumina.

The invention also concerns a catalyst containing at least one molecular sieve selected from the group formed by SAPO-31, SAPO-11, Theta-1, EU-1, omega zeolite, mordenite, ferrierite, Nu-10, Nu-86 and Nu-87, said sieve having been subjected to the coking treatment described above to render it selective.

The treatment is preferably carried out at a pressure of 0.1–0.5 MPa, between 400° C. and 535° C., in the absence of hydrogen and using at least one olefin, polyolefin or an alkane containing 4 to 12 carbon atoms.

EXAMPLES

The following examples illustrate the invention without limiting its scope.

Isomerization performance was expressed as follows:

Butene conversion
$$C = \frac{S(\% \text{ n-butenes})\text{feed} - S(\% \text{ n-butenes})\text{effluent}}{S(\% \text{ n-butenes})\text{feed}} \times 100$$

Isobutene selectivity
$$S = \frac{(\% \text{ isobutene})\text{effluent} - (\% \text{ isobutene})\text{feed}}{S(\% \text{ n-butenes})\text{feed} - S(\% \text{ n-butenes})\text{effluent}} \times 100$$

3) Isobutene yield
$R = C \times S/100$

Example 1:

Catalyst 1, in accordance with the invention 10 g of ferrierite, with a pore size of 0.42 nm×0.54 nm and 0.35 nm×0.48 nm, synthesized using the method described in U.S. Pat. No. 4,853,203 and U.S. Pat. No. 4,982,046, in the acid form and with a Si/Al atomic ratio of 13.8, was pelletized then screened to obtain a fraction with a diameter which was in the range 0.2 mm to 0.5 mm, then 5 g of pelletized and sieved ferrierite was introduced into a tube reactor for use as a fixed bed.

This ferrierite was then calcined in dry air for 4 hours at 550° C. and then a coking pre-treatment was applied to it.

The pre-treatment consisted of introducing n-butenes (which also constituted the feed to be isomerized) at a temperature of 500° C. for 2 hours. The n-butenes were introduced diluted in nitrogen at the following partial pressures: $P_{n\text{-}butenes}$=0.2 bar and $P_{N2}$=0.8 bar, at a space velocity of 2 grams of n-butenes per gram of ferrierite per hour (2 h$^{-1}$).

The reactor temperature was reduced to 350° C. the temperature of the n-butene isomerisation reaction, and the wwh was held at 2 h$^{-1}$.

The n-butene conversion, isobutene selectivities and isobutene yields were measured after one hour of n-butene injection and are shown in Table 1.

Similar results were obtained with a catalyst constituted by 80% by weight of the zeolite used in this example and 20% by weight of alumina.

Example 2:

Catalyst 2, not in accordance with the invention

The same ferrierite as that used for Example 1 was used in the same procedure in a fixed bed reactor and calcined at 550° C. for 4 hours.

It then underwent pre-treatment which consisted of introducing n-butenes to be isomerized at a temperature of 120° C. for 2 hours. The n-butenes were introduced diluted in nitrogen at the following partial pressures: $P_{n\text{-}butenes}$=0.2 bar and $P_{N2}$=0.8 bar, at a space velocity of 2 grams of n-butenes per gram of ferrierite per hour (2 h$^{-1}$).

The reactor temperature was raised to 350° C., the temperature of the n-butene isomerization reaction, and the wwh was held at 2 h$^{-1}$.

The n-butene conversion, isobutene selectivities and isobutene yields were measured after one hour of n-butene injection and are shown in Table 1.

TABLE 1

|  | n-butene conversion (weight %) | Isobutene selectivity (weight %) | Isobutene yield (weight %) |
| --- | --- | --- | --- |
| Example 1 in accordance with invention | 45 | 90 | 40.5 |
| Example 2 not in accordance with invention | 50 | 60 | 30 |

The table shows the influence of pretreating the ferrierite in accordance with the invention on the isobutene selectivities and yields which in this case were higher than when no pre-treatment in accordance with the invention was applied.

Example 3:

catalyst 3, in accordance with the invention 10 g of ZSM-23 zeolite of structure type MTT, synthesized using the method described in European patent EP 347,273, in its acid form and with a Si/Al atomic ratio of 50, was pelletized, then screened to obtain a fraction with a diameter in the range 0.2 mm to 0.5 mm, then 5 g of pelletized and screened ZSM-23 was introduced into a tube reactor for use as a fixed bed.

This ZSM-23 zeolite was then calcined in dry air for 4 hours at 550° C. and then a coking pre-treatment was applied to it. The pre-treatment consisted of introducing n-butenes to be isomerized at a temperature of 500° C. for 2 hours. The n-butenes were introduced diluted in nitrogen at the following partial pressures: $P_{n\text{-}butenes}$=0.2 bar and $P_{N2}$=0.8 bar, at a space velocity of 2 grams of n-butenes per gram of ZSM-23 per hour (2 h$^{-1}$).

The reactor temperature was reduced to 350° C., the temperature of the n-butene isomerisation reaction, and the wwh was held at 2 h$^{-1}$.

The n-butene conversion, isobutene selectivities and isobutene yields were measured after one hour of n-butene injection and are shown in Table 2.

Similar results were obtained with a catalyst constituted by 80% by weight of the zeolite used in this example and 20% by weight of alumina.

Example 4:

catalyst 4, not in accordance with the invention

The same ZSM-23 zeolite as that used in Example 3 was used in the same procedure in a fixed bed reactor, and calcined at 550° C. for 4 hours.

It then underwent pre-treatment which consisted of introducing n-butenes to be isomerized at a temperature of 150° C. for 2 hours. The n-butenes were introduced diluted in nitrogen at the following partial pressures: $P_{n\text{-}butenes}$=0.2 bar and $P_{N2}$=0.8 bar, at a space velocity of 2 grams of n-butenes per gram of ZSM-23 per hour (2 h$^{-1}$).

The reactor temperature was then raised to 350° C., the temperature of the n-butene isomerization reaction, and the wwh was held at 2 h$^{-1}$.

The n-butene conversion, isobutene selectivities and isobutene yields were measured after one hour of n-butene injection and are shown in Table 2.

TABLE 2

|  | n-butene conversion (weight %) | Isobutene selectivity (weight %) | Isobutene yield (weight %) |
| --- | --- | --- | --- |
| Example 3 in accordance with invention | 46 | 40 | 18.4 |
| Example 4 not in accordance with invention | 52 | 20 | 10.4 |

The table shows the influence of a pretreating the ZSM-23 in accordance with the invention on the isobutene selectivities and yields which in this case were higher than when no pre-treatment in accordance with the invention was applied.

The preceding examples can be repeated with similar success by substituting the generically or specifically described reactants and/or operating condition of this invention for those used in the preceding examples.

The entire disclosure of all application, patents and publications, cited above and below, and of corresponding French application 95/05463, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for skeletal isomerization of an olefinic feed containing linear olefinic hydrocarbons containing 4 to 20 carbon atoms using a catalyst containing at least one molecular sieve with a pore size of 0.4 nm to 0.8 nm, said process comprising, prior to commencing the process, contacting said sieve with a pretreatment feed containing at least one hydrocarbon of 4 to 20 carbon atoms, said pretreatment feed being diluted in a inert gas, at a space velocity of 0.1–45 h$^{-1}$, a temperature of 300°–550° C., and at a pressure of 0.1–1 MPa for 0.5–48 h, whereby coke is deposited in said pores in said sieve, and then contacting said olefinic feed with the catalyst under skeletal isomerization conditions.

2. A process according to claim 1, wherein the hydrocarbon in said pretreatment feed contains 4 to 12 carbon atoms.

3. A process according to claim 1 wherein the hydrocarbon in said pretreatment feed is a monoolefin, polyolefin or an alkane.

4. A process according to claim 1 wherein the hydrocarbon in said pretreatment feed is diluted in nitrogen.

5. A process according to claim 1 wherein the skeletal isomerization temperature is 400° C. to 535° C., the pressure is 0.1 MPa to 9.5 MPa, the space velocity is 0.5 h$^{-1}$ to 25 h$^{-1}$ and the duration is 0.5 h to 24 h.

6. A process according to claim 1 wherein the molecular sieve has a pore size 0.4 nm to 0.7 nm.

7. A process according to claim 1 wherein the molecular sieve includes a one-dimensional microporous network.

8. A process according to claim 1 wherein the molecular sieve is ferrierite, SAPO-31, SAPO-11, Theta-1, EU-1, ZSM-12, ZSM-23, omega zeolite, mordenite, Nu-10, Nu-86 or Nu-87.

9. A process according to claim 1 wherein the catalyst further contains a matrix and wherein the molecular sieve is contacted with the pretreatment feed before combination with the matrix.

10. A process according to claim 1 wherein the molecular sieve is contacted with the pretreatment feed after combination with the matrix.

11. A process according to claim 1 wherein the sieve is contacted with the pretreatment feed outside the reaction zone.

12. A process according to claim 2, in which the skeletal isomerization conditions comprise a temperature of 150°–500° C., a pressure of 0.01–1 MPa, and at a space velocity of 0.1–10 h$^{-1}$.

13. A process according to claim 1 wherein the olefinic feed is an olefinic C$_4$ feed.

14. A process according to claim 1, wherein the olefinic feed is an olefinic C$_5$ feed.

15. A process for skeletal isomerisation of a feed containing linear olefinic hydrocarbons containing 4 to 20 carbon atoms, comprising contacting said feed with a catalyst prepared by a process wherein a zeolitic molecular sieve with a pore size of 0.4 nm to 0.8 nm is contacted with a feed containing at least one hydrocarbon of 4 to 20 carbon atoms, diluted in an inert gas, at a space velocity of 0.1–45 h$^{-1}$, a temperature of 300°–550° C., and at a pressure of 0.1–1 MPa for 0.5–48 h. whereby coke is deposited in said pores in said sieve.

16. A process for skeletal isomerisation of a feed containing linear olefinic hydrocarbons containing 4 to 20 carbon atoms, comprising contacting said feed under isomerization conditions with a catalyst prepared by a process wherein a zeolitic molecular sieve selected from the group consisting of ferrierite, Theta-1, EU-1, omega zeolite, mordenite, Nu-10, Nu-86 and Nu-87, is contacted with a feed containing at least one hydrocarbon of 4 to 20 carbon atoms, diluted in an inert gas, at a space velocity of 0.1–45 h$^{-1}$, a temperature of 300°–550° C., and at a pressure of 0.1–1 MPa for 0.5–48 h, whereby coke is deposited in said pores in said sieve.

17. A process for skeletal isomerization of an olefinic feed containing linear olefinic hydrocarbons containing 4 to 20 carbon atoms using a catalyst containing at least one zeolitic molecular sieve with a pore size of 0.4 nm to 0.8 nm, said process comprising, prior to commencing the process, contacting said sieve with a pretreatment feed containing at least one hydrocarbon of 4 to 20 carbon atoms, at a space velocity of 0.1–45 h$^{-1}$, a temperature of 300°–550° C., and at a pressure of 0.1–1 MPa for 0.5–48 h, whereby coke is deposited in said pores in said sieve, and then contacting said olefinic feed with the catalyst under isomerization conditions.

18. A process according to claim 17, wherein said pretreatment feed is diluted in an inert gas.

19. A process according to claim 1 wherein the molecular sieve is ferrierite, Theta-1, EU-1, ZSM-12, ZSM-23, omega zeolite, mordenite, Nu-10, Nu-86 or Nu-87.

* * * * *